US00PP08814P

United States Patent [19]

Austin

[11] Patent Number: Plant 8,814

[45] Date of Patent: Jul. 5, 1994

[54] ROSE PLANT NAMED 'AUSCLUB'

[75] Inventor: David C. H. Austin, Albrighton, England

[73] Assignee: David Austin Roses Limited, Albrighton, England

[21] Appl. No.: 955,911

[22] Filed: Sep. 30, 1992

[51] Int. Cl.[5] ..... A01H 5/00

[52] U.S. Cl. ..... Plt./1

[58] Field of Search ..... Plt. 1, 26

*Primary Examiner*—Howard J. Locker
*Assistant Examiner*—E. F. McElwain
*Attorney, Agent, or Firm*—Klarquist, Sparkman, Campbell, Leigh & Whinston

[57] ABSTRACT

Rose plant of the shrub type having pink flowers paler than those of Mary Rose but darker than those of Chaucer and having glossy foliage.

1 Drawing Sheet

The present invention relates to a new and distinct variety of shrub rose plant of the *Rosa hybrida* class which was originated by me by crossing the variety Mary Rose, with the variety Chaucer.

The primary objective of this breeding was to produce a new shrub rose variety having pale, pink, quartered, scented flowers on a bushy plant and which repeat flowers. The objective was substantially achieved along with other desirable improvements as evidenced by the following unique combination of characteristics which are outstanding in the new variety and which distinguish it from its parents, as well as from all other varieties of which I am aware:

1. Paler pink flowers than Mary Rose;
2. Darker flowers than Chaucer; and
3. Glossy foliage.

Asexual reproduction of this new variety by budding, as performed at Albrighton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated.

Parentage:

*Seed parent.*—Mary Rose.

*Pollen parent.*—Chaucer.

Classification:

*Botanical.*—*Rosa hybrida.*

*Commercial.*—Shrub.

FLOWER

Observations made from specimens grown in a garden environment in Albrighton, England in August 1991.

Blooming habit: Recurrent.

Bud:

*Size.*—1" long when the petals start to unfurl.

*Form.*—The bud form is globular with cuspidate apex.

*Color.*—When sepals first divide, the bud color is Madder red 11B8. When half blown, the upper sides of the petals are pale red 12A3 with the top edge fading to Yellow white at the center of the petal; and the lower sides of the petals are the same as the upper side.

*Sepals.*—Color: Greyish green 29D7 with Violet brown blush 10E7 on margins and midline. Surface texture: Leathery, speckled with red glandular hairs. There are three normally appendaged sepals. There are two unappendaged sepals with hairy edges.

*Receptacle.*—Color: Greyish green 29E7. Shape: Goblet shaped. Size: $\frac{1}{4}'' \times \frac{1}{4}''$. Surface: Smooth.

*Peduncle.*—Length: Medium, very variable — 1–$1\frac{1}{2}''$. Surface: Glandular. Color: Medium green, bronzy 29D7 with violet brown blush 10E7. Strength: Erect.

Bloom:

*Size.*—Average open size is 3–4" in diameter.

*Borne.*—Singly, several together, in clusters of up to 15 flowers, very variable; Irregular shape.

*Stems.*—Medium. Average length is about 24 to 30 inches.

*Form.*—When first open: Cupped. Permanence: Flattens, outer petals curl back.

*Petalage.*—Number of petals under normal conditions: 60 to 80.

*Color.*—The upper side of the petals is Pale red 11A3 to 12A3, the top edge of petal fading to Yellow/white 1A2 at the center of petal. The reverse side of the petals is same as above. The color of the base of petals is Pale yellow 1A4. The major color on the upper side is Pale red 11A3 to 12A3.

*Variegations.*—None.

*Discoloration.*—The general tonality at the end of the first day: Slightly paler. At the end of the third day, top edge of petal is Reddish white 12A2 fading to White 1A1 at center.

*Fragrance.*—Moderate, delicate tea rose.

Petals:

*Texture.*—Thin, soft and silky.

*Shape.*—Round, oval, apex sightly recurved.

*Form.*—Deeply cupped, inner petal edges are slightly quilled.

*Arrangement.*—Informal, inner petals are crushed and folded, with few petaloids in the center.

*Persistence.*—Petals drop off cleanly before drying.

*Lastingness.*—On the plant: Long, 7 to 10 days. As a cut flower: Long, 5 to 7 days.

Reproductive parts:

*Anthers.*—Size: Medium, brood (⅛") perigynous zone. Quantity: Many. Color: Deep yellow 4A8. Arrangement: Regular around the styles, mixed with petaloids

*Filaments.*—Color: White 3A3 pale yellow.

*Pollen.*—Color: Golden yellow.

*Styles.*—Color: Pale yellow 1A3.

*Stigmas.*—Color: Pale yellow 2A3.

Form: Shrub.

Height: 36 to 42 inches.

Growth: Medium, branching.

Foliage:

*Number of leaflets on normal mid-stem leaves.*—7.

*Size.*—Medium to large, about 1½"-3¼" long and 1½"-2" wide.

*Quantity.*—Normal.

*Color.*—New foliage: Dark green 29F7 with Violet brown blush 10E8. Old foliage: Dark green 28F7.

Leaflets:

*Shape.*—Oval, cuspidate tip, pointed oval.

*Texture.*—Upper side: Glossy.

*Edge.*—Serrated.

*Serration.*—Single, small.

*Petiole rachis.*—Color: Green, reddish, 29F7 dark green with violet brown blush.

*Petiole underside.*—With prickles, 0 to 2 per internode.

*Stipules.*—Medium, about 1" long.

*Disease resistance.*—Resistance to mildew and blackspot under normal growing conditions at Albrighton, Wolverhampton, England.

Wood:

*New wood.*—Color: Bracken green 29E7. Bark: Smooth.

*Old wood.*—Color: Deep green 29E8. Bark: Smooth, slightly ridged.

Prickles:

*Quantity.*—On main canes from base: Many. On laterals from main canes: Many.

*Form.*—Medium, straight.

*Color when young.*—Green and red, greyish yellow, evenly spaced.

Small prickles:

*Quantity.*—On main stalks: Many on main stalks. On laterals: Many on laterals.

I claim:

1. A new and distinct variety of shrub rose plant of the *Rosa hybrida* class, substantially as herein shown and described, characterized particularly as to novelty by the unique combination of its pink flowers paler than those of Mary Rose but darker than those of Chaucer and having glossy foliage.

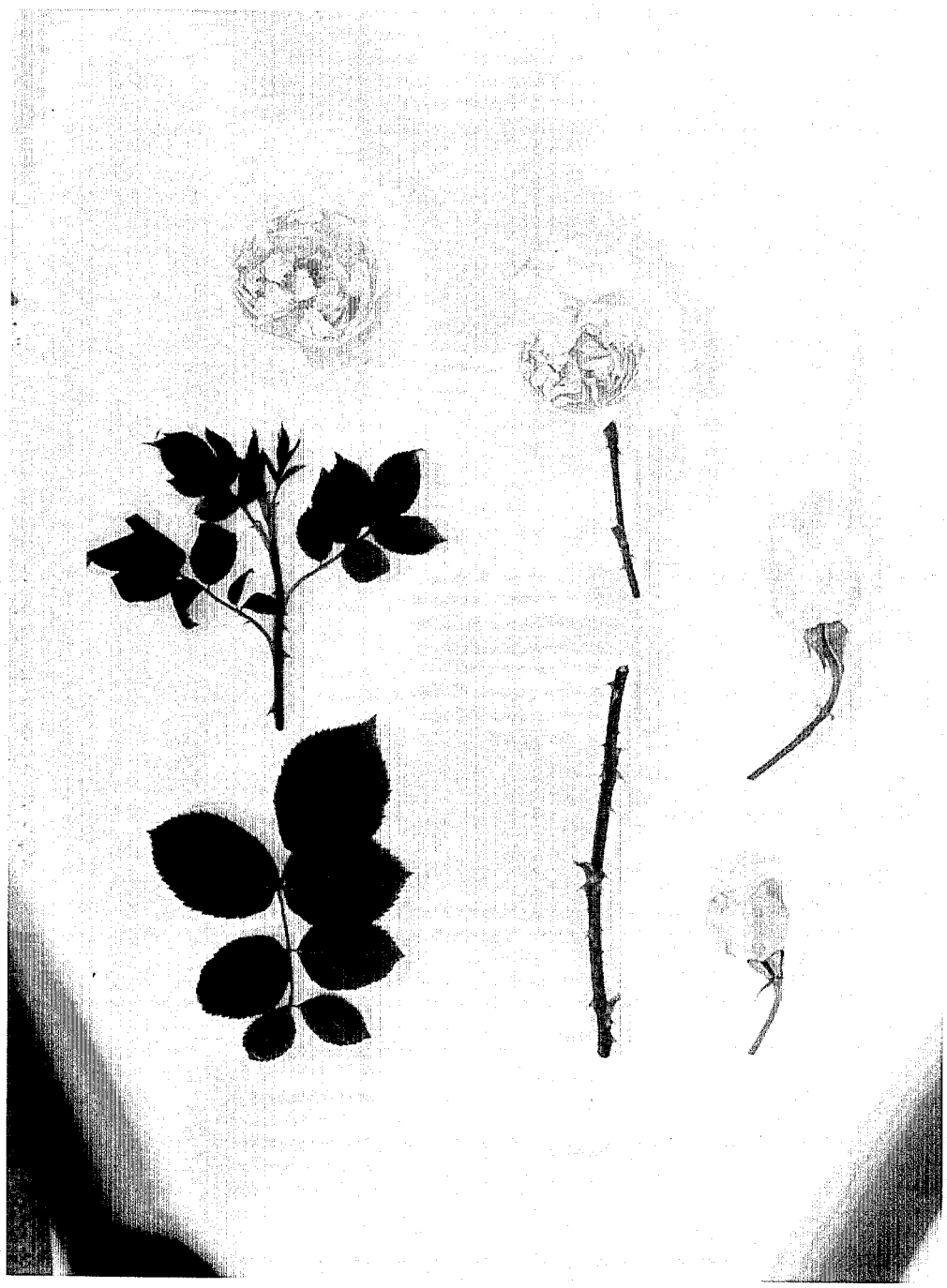

* * * * *